(12) United States Patent
Fitzgerald

(10) Patent No.: US 6,958,054 B2
(45) Date of Patent: Oct. 25, 2005

(54) INTRAVENOUS CATHETER DEVICE

(75) Inventor: Lisa M. Fitzgerald, Sarasota, FL (US)

(73) Assignee: P. Rowan Smith, Houston, TX (US)

( * ) Notice: Subject to any disclaimer, the term of this patent is extended or adjusted under 35 U.S.C. 154(b) by 8 days.

(21) Appl. No.: 10/765,666

(22) Filed: Jan. 28, 2004

(65) Prior Publication Data

US 2005/0165355 A1 Jul. 28, 2005

(51) Int. Cl.$^7$ .............................................. A61M 5/32
(52) U.S. Cl. .................. 604/162; 604/263; 604/164.08
(58) Field of Search ........................ 604/110, 263, 158, 604/162, 192, 197, 198, 164.08, 168.01, 604/165.01, 165.02; 128/919

(56) References Cited

U.S. PATENT DOCUMENTS

| | | | |
|---|---|---|---|
| 3,262,449 A * | 7/1966 | Pannier, Jr. et al. ........ | 604/159 |
| 4,781,692 A * | 11/1988 | Jagger et al. .......... | 604/164.08 |
| 4,850,961 A * | 7/1989 | Wanderer et al. ........... | 604/508 |
| 4,994,042 A * | 2/1991 | Vadher ................... | 604/165.01 |
| 5,019,049 A | 5/1991 | Haining | |
| 5,176,650 A | 1/1993 | Haining | |
| 5,279,579 A * | 1/1994 | D'Amico ..................... | 604/192 |
| 5,279,590 A * | 1/1994 | Sinko et al. ................ | 604/263 |
| 5,312,359 A * | 5/1994 | Wallace .................. | 604/164.08 |
| 5,462,533 A * | 10/1995 | Daugherty ............. | 604/164.01 |
| 5,893,844 A * | 4/1999 | Misawa ....................... | 604/195 |
| 5,951,523 A * | 9/1999 | Osterlind et al. ........... | 604/192 |
| 6,537,253 B1 * | 3/2003 | Haindl ........................ | 604/158 |
| 6,641,555 B1 * | 11/2003 | Botich et al. ............... | 604/110 |
| 2002/0045843 A1 * | 4/2002 | Barker et al. ............... | 600/585 |

* cited by examiner

Primary Examiner—Cris L. Rodriguez
(74) Attorney, Agent, or Firm—Richard L. Moseley

(57) ABSTRACT

A catheter device is disclosed which the hypodermic needle used for insertion is retracted into a protective sheath and left in place during use. An IV fluid flow path is provided that is blocked by the hypodermic needle prior to retraction but is opened by the retraction of the needle from the catheter. The insertion hypodermic needle is not discarded separately but only after the use of the whole catheter device to inject fluids.

9 Claims, 8 Drawing Sheets

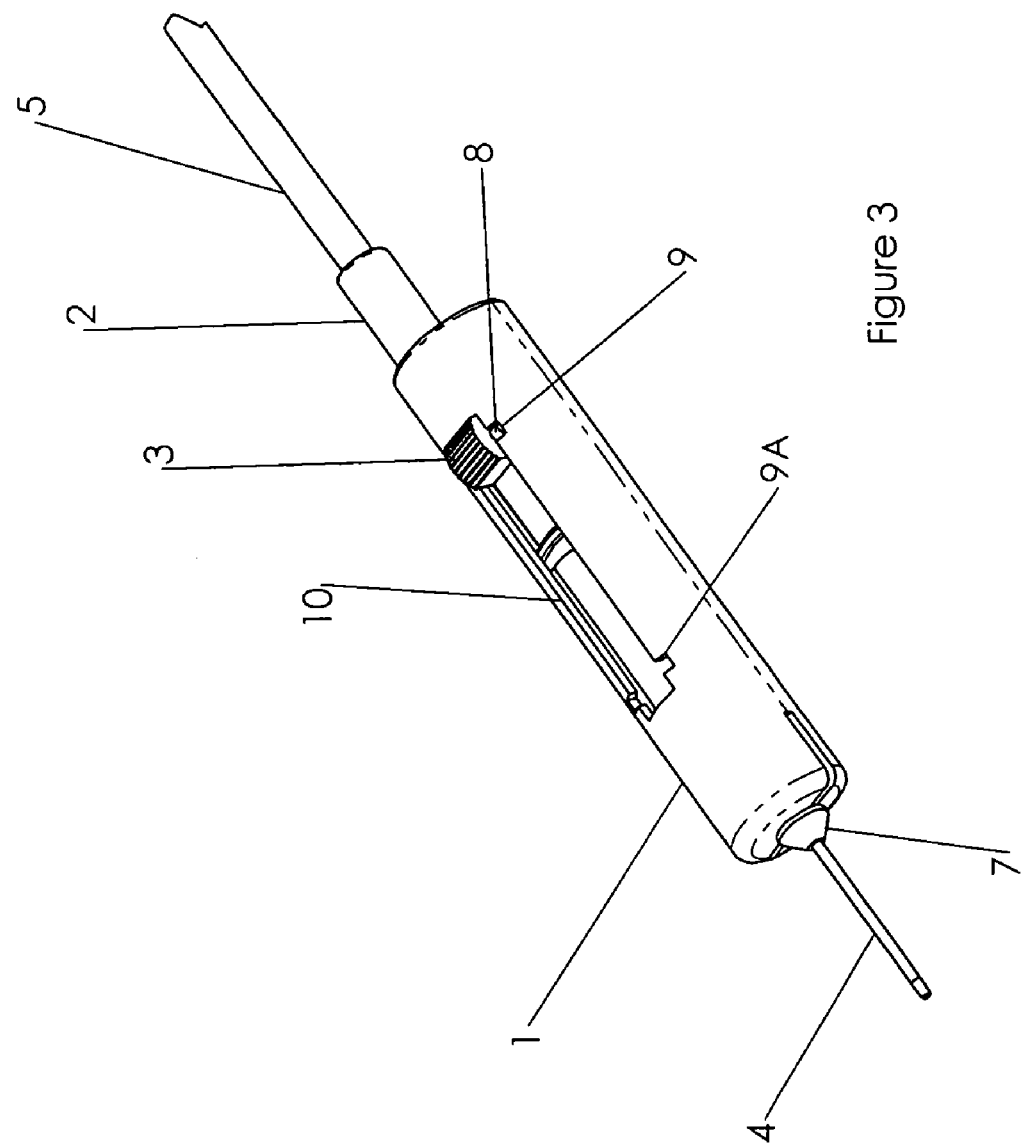

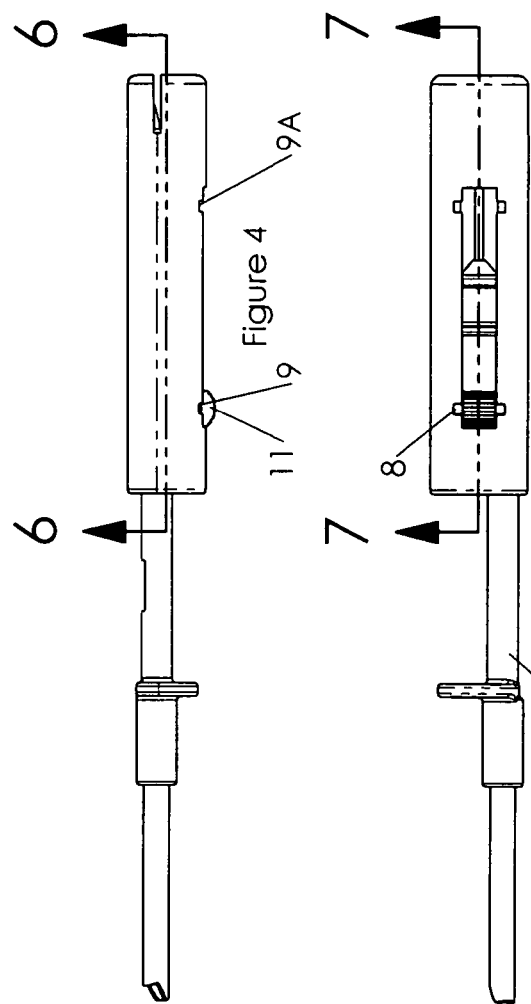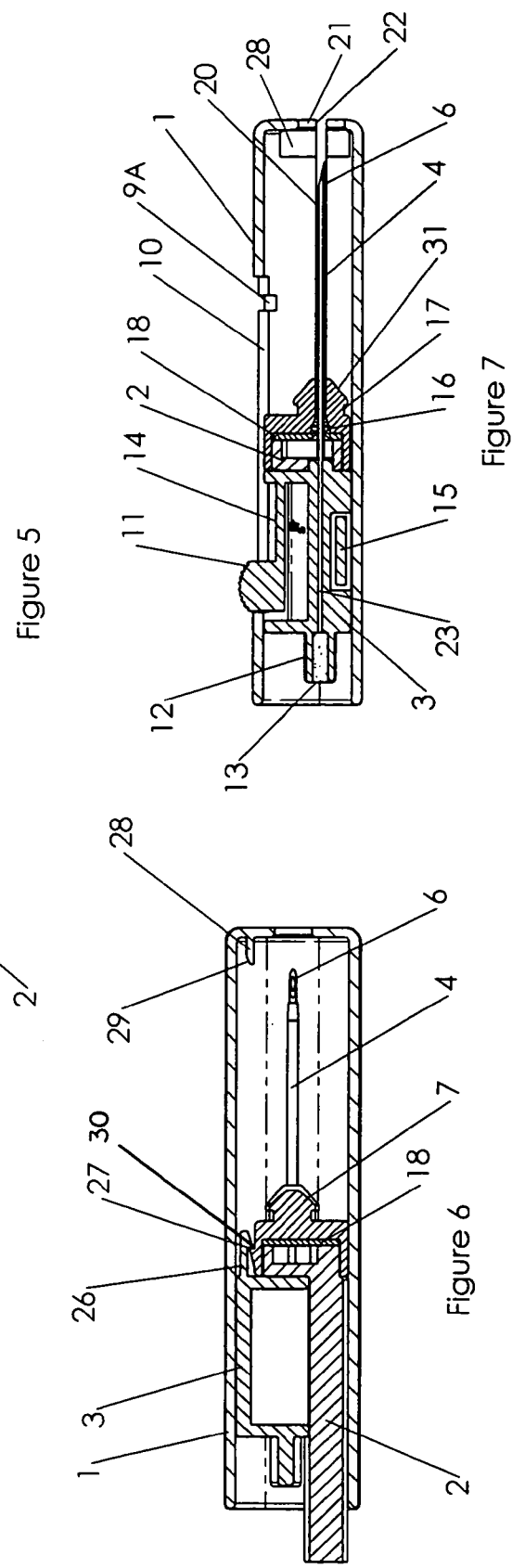

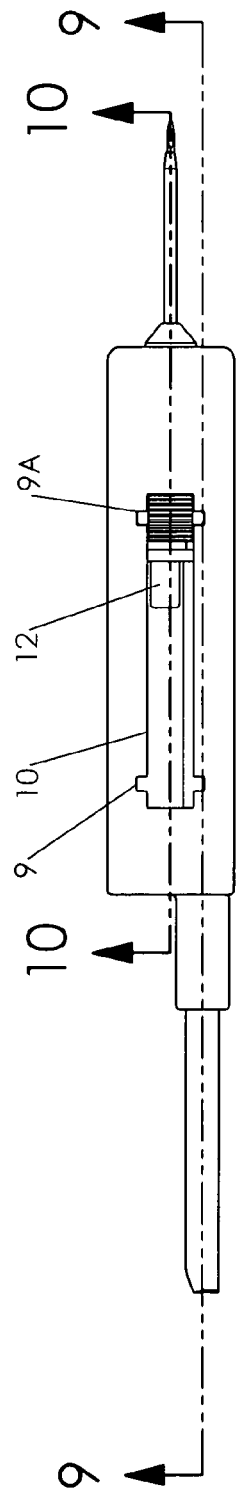
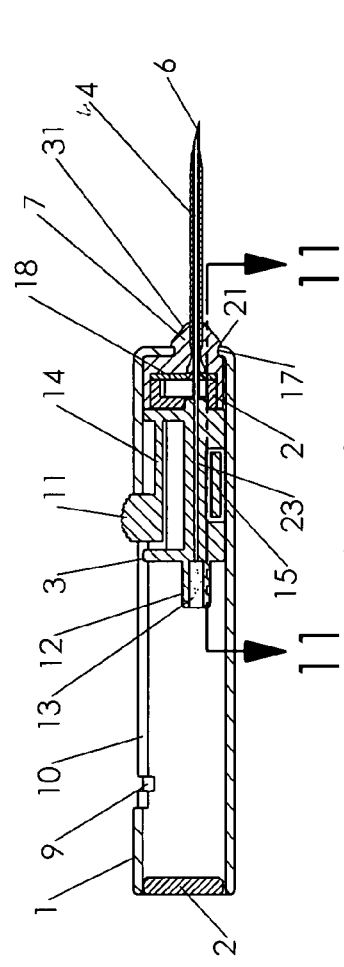
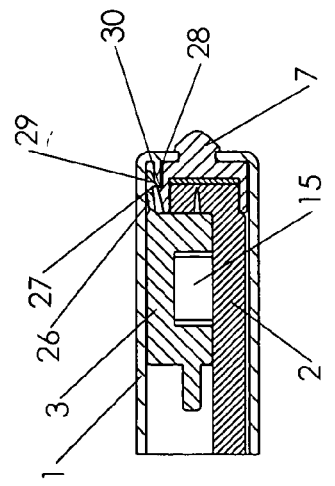
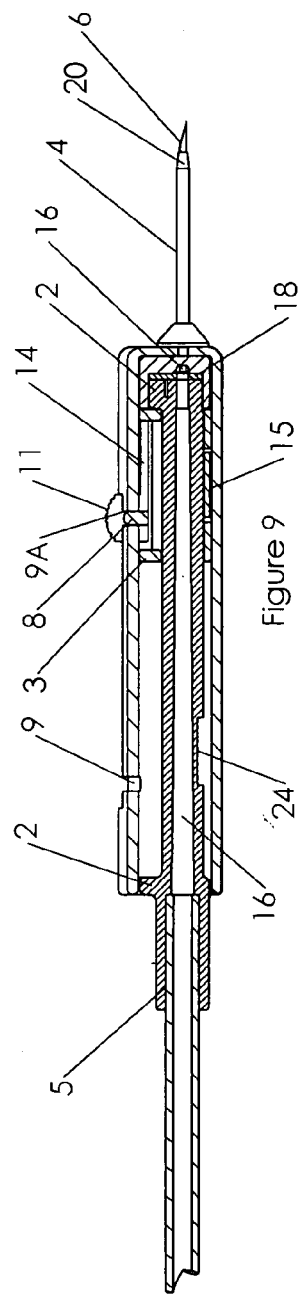

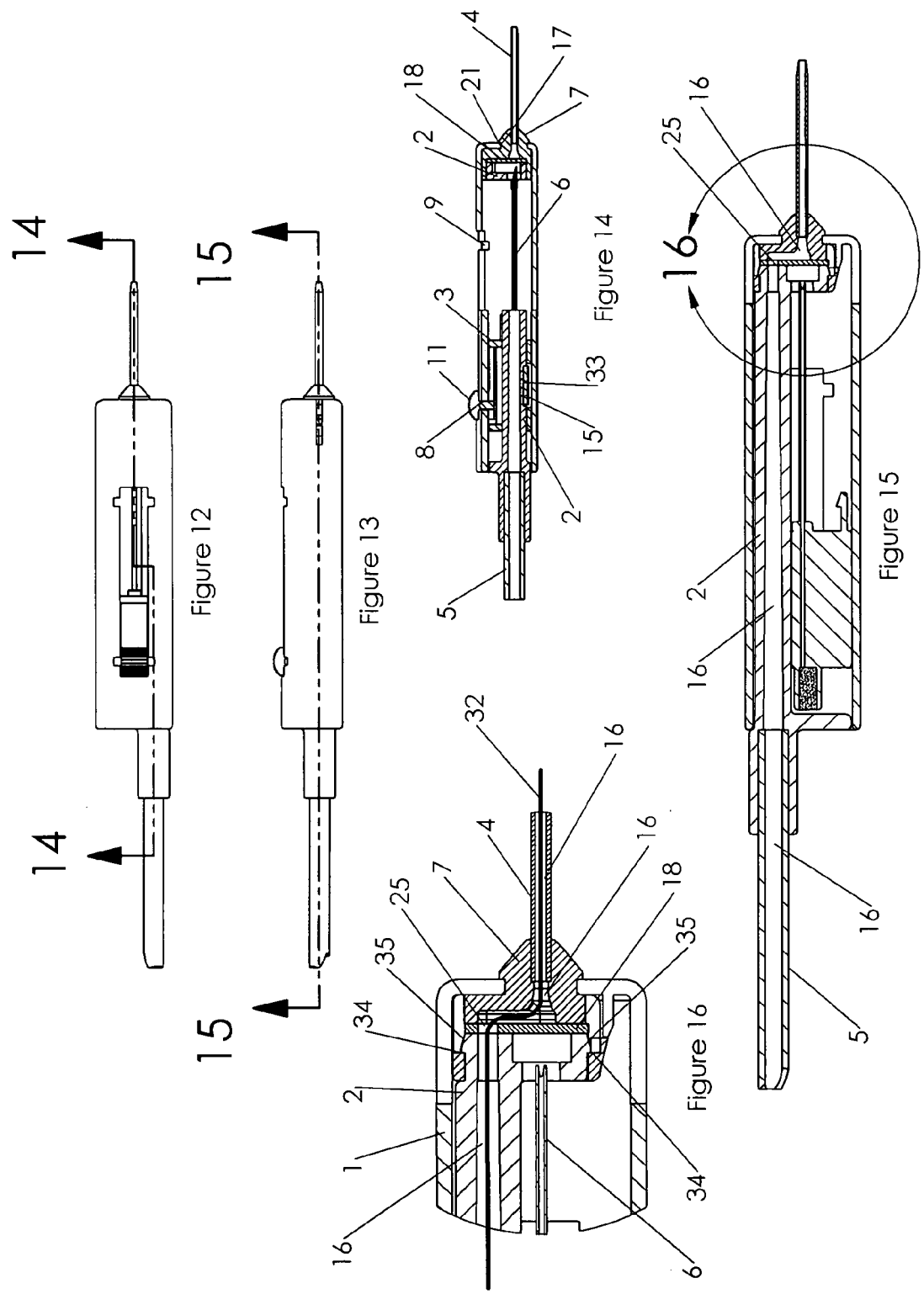

INTRAVENOUS CATHETER DEVICE

BACKGROUND OF THE INVENTION

1. Field of the Invention

The present invention relates to a device for the insertion of a flexible catheter into a vein of a patient for intravenous administration of fluids. More Particularly the invention relates to devices wherein the flexible catheter is inserted into the vein by a sharp needle about which the catheter is snugly mounted, and the needle and catheter are inserted into the vein and the needle retracted leaving the catheter in place. More particularly the invention relates to a catheter insertion device wherein the insertion needle is retractable into the device after removal. Most particularly the invention relates to a catheter insertion device with an integral IV port wherein the insertion device is directly connected to the IV fluid source.

2. Related Art

The development of flexible intravenous catheters has greatly increased the comfort of patients during intravenous administration of medicinal fluids. The flexible catheter prevents unwanted puncture of the vein. The flexible catheter normally consists of a narrow tube of NYLON or TEFLON construction with a rigid member attached at the rear end for connection to the source of fluid to be administered.

Because the catheter is flexible it cannot by itself be inserted into the vein. Therefore, the catheter is snugly nested about a sharp hypodermic type needle which can be inserted into the vein. After insertion the sharp needle is withdrawn leaving the catheter in place for connection to the fluid source. The insertion needle is usually discarded as it is intended for a single use only. Often the needle is discarded in a careless manner leaving the exposed needle point as a hazard.

Accidental needle prick has been a problem for years in the health care industry. However, the advent of the HIV or AIDS virus has focused attention on the problem. While several diseases, such as viral hepatitis, may be contracted from bodily fluids of infected persons, HIV has caused the most concern because to date no preventative or cure is known. Protection against accidental needle prick is expected to remain a concern even after a vaccine or cure is found, an ounce of prevention being worth a pound of cure.

Earlier U.S. Pat. Nos. 5,019,019 and 5,176,650 have addressed this problem in regard to catheter insertion devices.

SUMMARY OF THE INVENTION

To protect against accidental needle prick a catheter and insertion device are provided wherein the needle is retractable within the device after insertion of the catheter. The device comprises a hollow barrel or tube of semi-rigid plastic material into which the needle can be retracted after use. The insertion needle is mounted on a carrier with the sharp end oriented toward the insertion end of the barrel with the catheter snugly fit about the needle. A sliding tab is mounted to the carrier by an outwardly biased flexible member and extends through a longitudinal sliding track in the barrel. Near either end of the sliding track notches to engage locking hubs on the sliding tab to releasably lock the carrier in either the exposed or retracted position. The catheter and catheter carrier are secured to the needle carrier by a releasable latch that is released when the needle, needle carrier, catheter and catheter carrier are in the fully exposed position. A retainer ring holds the catheter carrier and catheter in position after retraction of the needle and needle carrier. The needle is retained inside the device during in use.

BRIEF DESCRIPTION OF THE DRAWING

FIG. 3 shows the device after the catheter has been inserted and the hypodermic needle retracted.

FIG. 4 is a side plan view of the device with the catheter and needle in the retracted position.

FIG. 5 is a top plan view of the device with the catheter and needle in the retracted position.

FIG. 6 is a cross sectional view taken along line 6—6 of FIG. 4.

FIG. 7 is a cross sectional view taken along line 7—7 of FIG. 5.

FIG. 8 is top plan view of the device with the catheter and needle in the exposed position.

FIG. 9 is a cross sectional view of the device taken along line 9—9 of FIG. 8.

FIG. 10 is a cross sectional view of the device taken along line 10—10 of FIG. 8.

FIG. 11 is a cross sectional view taken along line 11—11 of FIG. 10.

FIG. 12 is a top plan view of the device with the catheter in the exposed position with the hypodermic needle retracted.

FIG. 13 is a side plan view of the device with the catheter in the exposed position with the hypodermic needle retracted.

FIG. 14 is a cross sectional view of the device taken along line 14—14 in FIG. 12.

FIG. 15 is a cross sectional view of the device taken along line 15—15 in FIG. 12.

FIG. 16 is an enlarged view of the area circled in FIG. 15.

DESCRIPTION OF THE PREFERRED EMBODIMENTS

Figure 1:
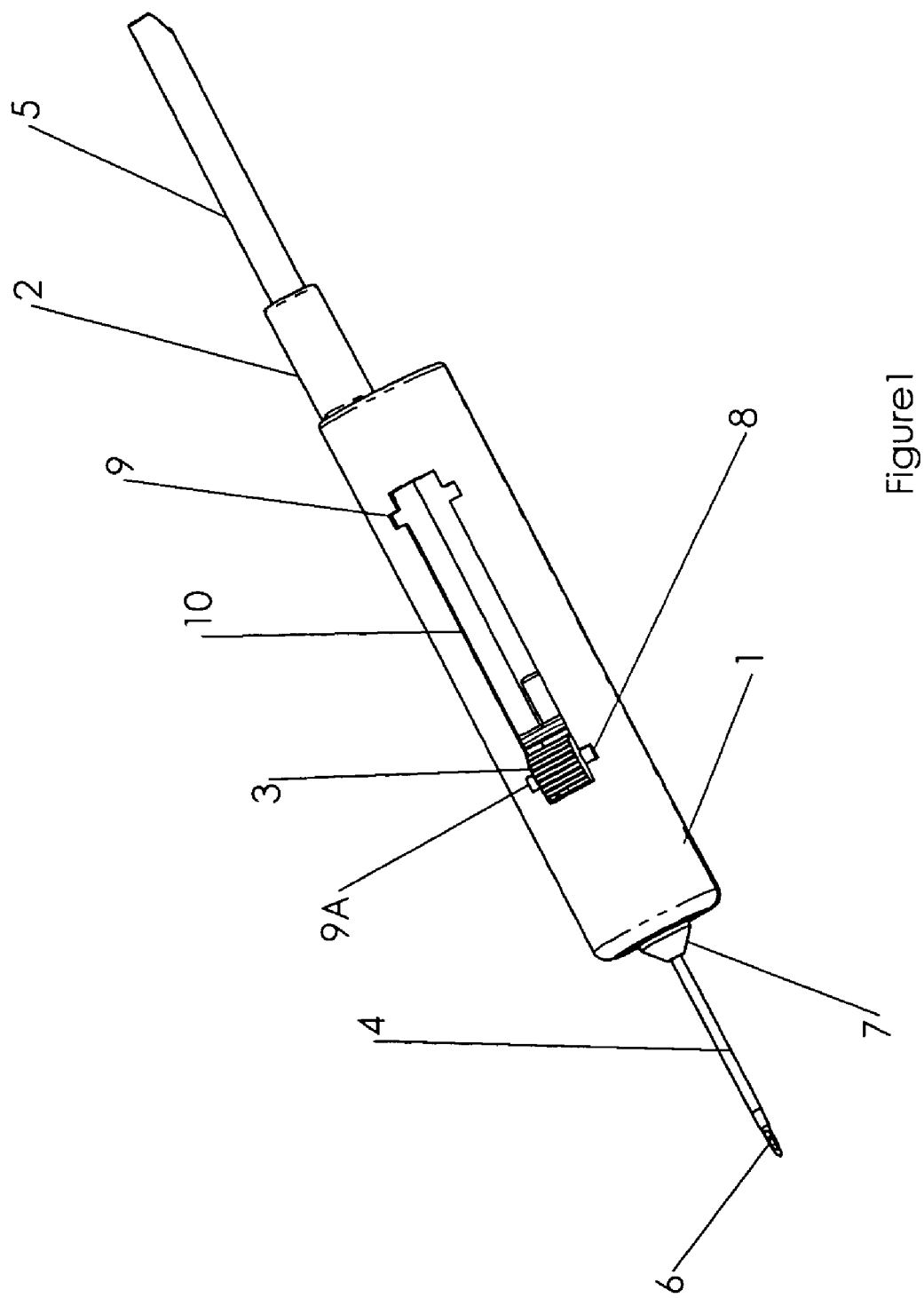
FIG. 1 shows the device ready for insertion into a vein with the hypodermic needle and catheter fully exposed.

For a detailed description of the preferred embodiment the reader is referred to the appended figures in which like components are given like numerals for ease of reference.

For quick reference all of the reference numerals are listed in Table I below and their corresponding parts identified with the figures in which the parts are identified. The parts may be shown in other figures but are identified by the reference numerals in the listed figures only.

TABLE I

| Ref. No. | Description | Identified in Figure Number: |
| --- | --- | --- |
| 1 | protective sheath | 1–3, 6–7, 10–11, 16–18 |
| 2 | port body | 1–3, 5, 9–11, 14–18 |
| 3 | needle carrier | 1–3, 6–7, 9–11, 14, 17–18 |
| 4 | catheter | 1, 3, 6–7, 9–10, 14, 16–18 |
| 5 | IV tube | 1–3, 9, 14–15, 17–18 |
| 6 | hypodermic needle | 1, 6–7, 9–10, 14, 16–18 |
| 7 | catheter carrier | 1–3, 6, 10–11, 14, 16–18 |
| 8 | needle locking tab | 1–3, 5, 9, 14, 17–18 |

TABLE I-continued

| Ref. No. | Description | Identified in Figure Number: |
|---|---|---|
| 9 | needle locking slot | 1–4, 8–10, 14, 17, 18 |
| 9A | needle locking slot | 1–4, 7–9, 17–18 |
| 10 | needle carrier track | 1–3, 7–8, 10, 17–18 |
| 11 | actuator | 4, 7, 9–10, 14, 17–18 |
| 12 | flashback sight tube | 7–8, 10, 17–18 |
| 13 | indicator | 7–8, 17–18 |
| 14 | actuator spring | 7, 9–10, 17–18 |
| 15 | rear retainer ring | 7, 10–11, 14, 18 |
| 16 | flow cavity | 7, 9, 15–16 |
| 17 | catheter retainer slot | 7, 10, 14, 17–18 |
| 18 | membrane | 6–7, 9–10, 14, 16, 18 |
| 19 | needle carrier slot | 18 |
| 20 | catheter taper | 7, 9, 18 |
| 21 | catheter carrier retainer ring | 7, 10, 14, 17–18 |
| 22 | retainer ring relief slot | 7, 17–18 |
| 23 | flashback blood path | 7, 10 |
| 24 | needle retainer notch | 9 |
| 25 | membrane aperture | 16 |
| 26 | forward retainer spring | 6, 11, 17–18 |
| 27 | forward locking surface | 6, 11, 17–18 |
| 28 | needle carrier release tab | 6–7, 11 |
| 29 | needle carrier release ramp | 6, 11 |
| 30 | forward catheter locking surface | 6, 11 |
| 31 | conical ramp | 7, 10–11, 18 |
| 32 | IV liquid flow path | 16 |
| 33 | rear retainer slot | 14 |
| 34 | port body retainer surface | 16, 18 |
| 35 | locking ramp | 16, 18 |

Figure 17:
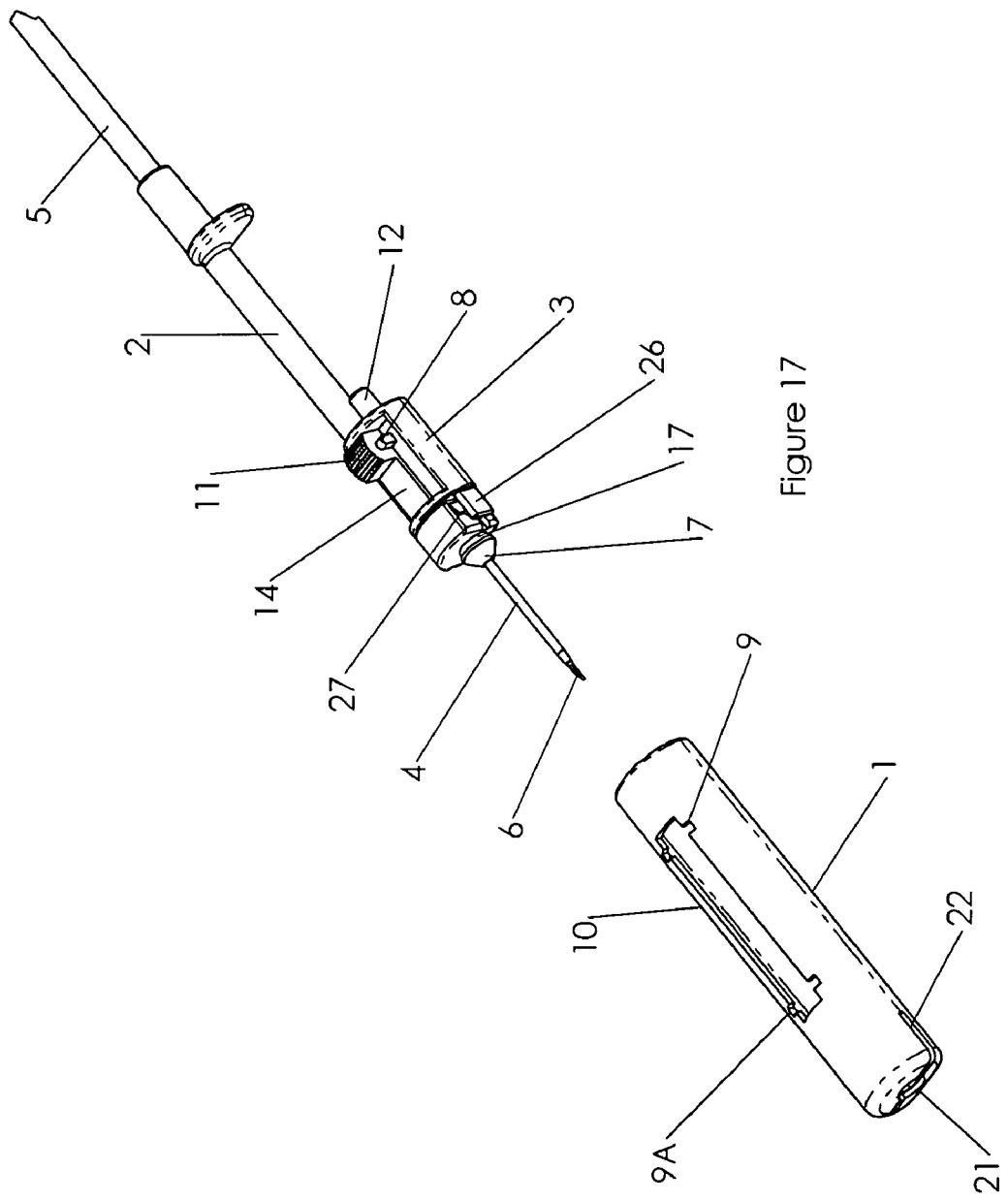
FIG. 17 is a perspective exploded view of the device form the right side.
Figure 18:
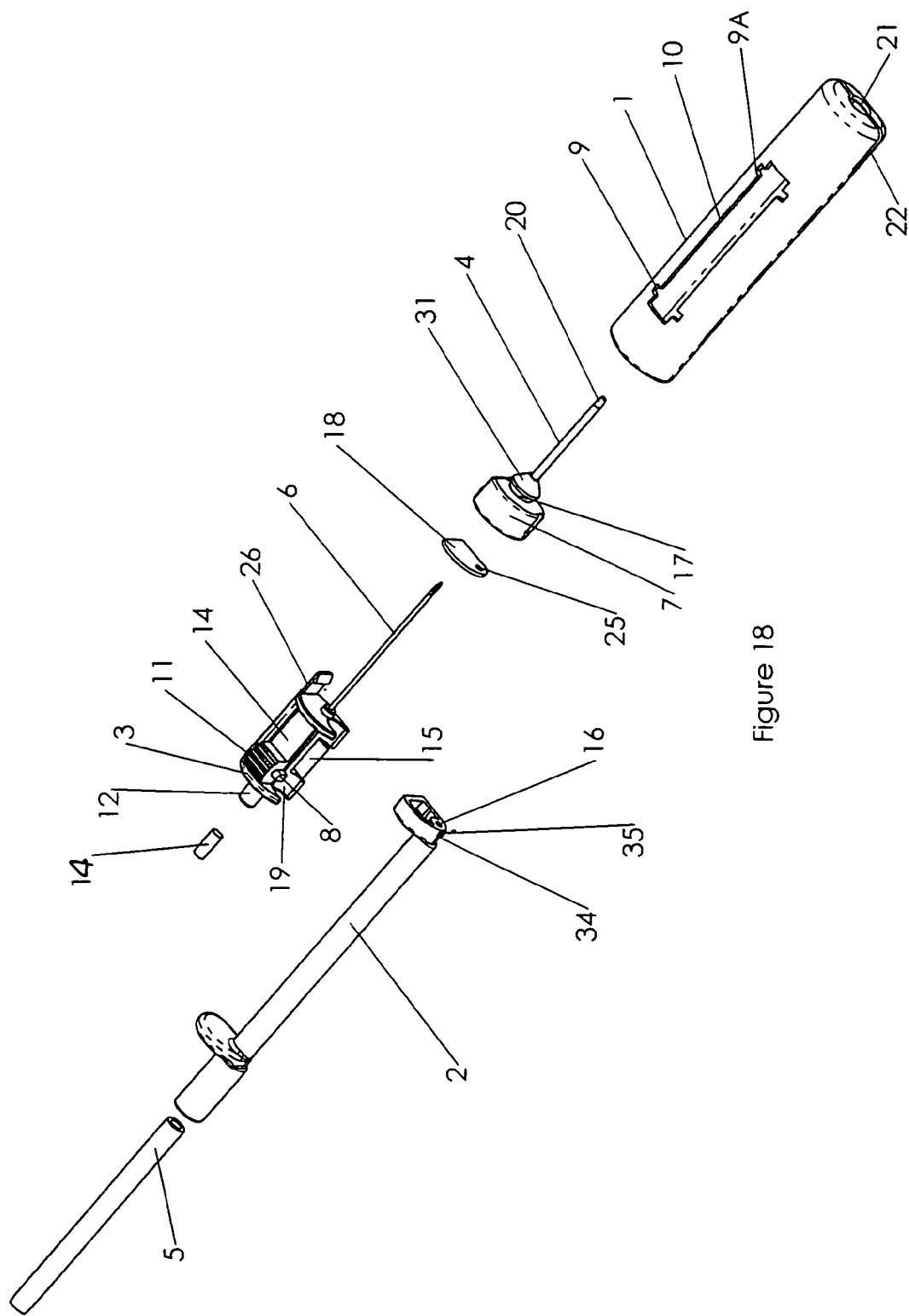
FIG. 18 is a perspective exploded view of the device form the left side.

Referring first o FIGS. 17 and 18 the components of the catheter device are seen in exploded views. The device is seen to comprise a protective sheath 1 having a longitudinal slot or needle carrier track 10 on one surface with needle locking slots 9 and 9A near either end of the carrier track 10. The catheter is seen to have a near quarter round cross sectional or tear drop area with the needle and catheter in the largest area and adjacent the flat for ease of use and insertion of the needle and catheter (this can best be seen by looking at the internal parts which conform to the cross sectional area of the sheath such as membrane 18 and port body retaining surface). A catheter retaining ring 21 and retaining ring slot 22 are located at the proximal end along with an aperture through which the hypodermic needle and catheter may be exposed. The catheter 4 and catheter carrier 7 are mounted on the needle carrier 3 with membrane 18 between the two. As assembled for shipment the hypodermic pierces the membrane 18 and fits into the catheter 4. On top of the needle carrier 3 is actuator 11 which is connected to the needle carrier 3 by actuator spring 14. On either side of actuator 11 are needle locking tabs 8 which may engage needle locking slots 9 and 9A. At the rear of the needle carrier 3 is flashback sight tube 12 which contains flashback indicator 13. located alongside needle carrier 3 is port body 2 having flow cavity 16 which is aligned with membrane aperture 25. The IV fluid tube 5 is connected to the port body.

Referring now to the FIG. 1 the device is shown in perspective view in the ready mode with the catheter 4, catheter carrier 7 and hypodermic needle 6 fully extended from the sheath 1 with the hypodermic needle 6 locked into this position by the needle locking tab 8 engaging the needle locking slot 9A. The IV tube 5 is shown connected to the port body 2. The needle carrier 3 is shown extending through the needle carrier track 10.

Figure 2:
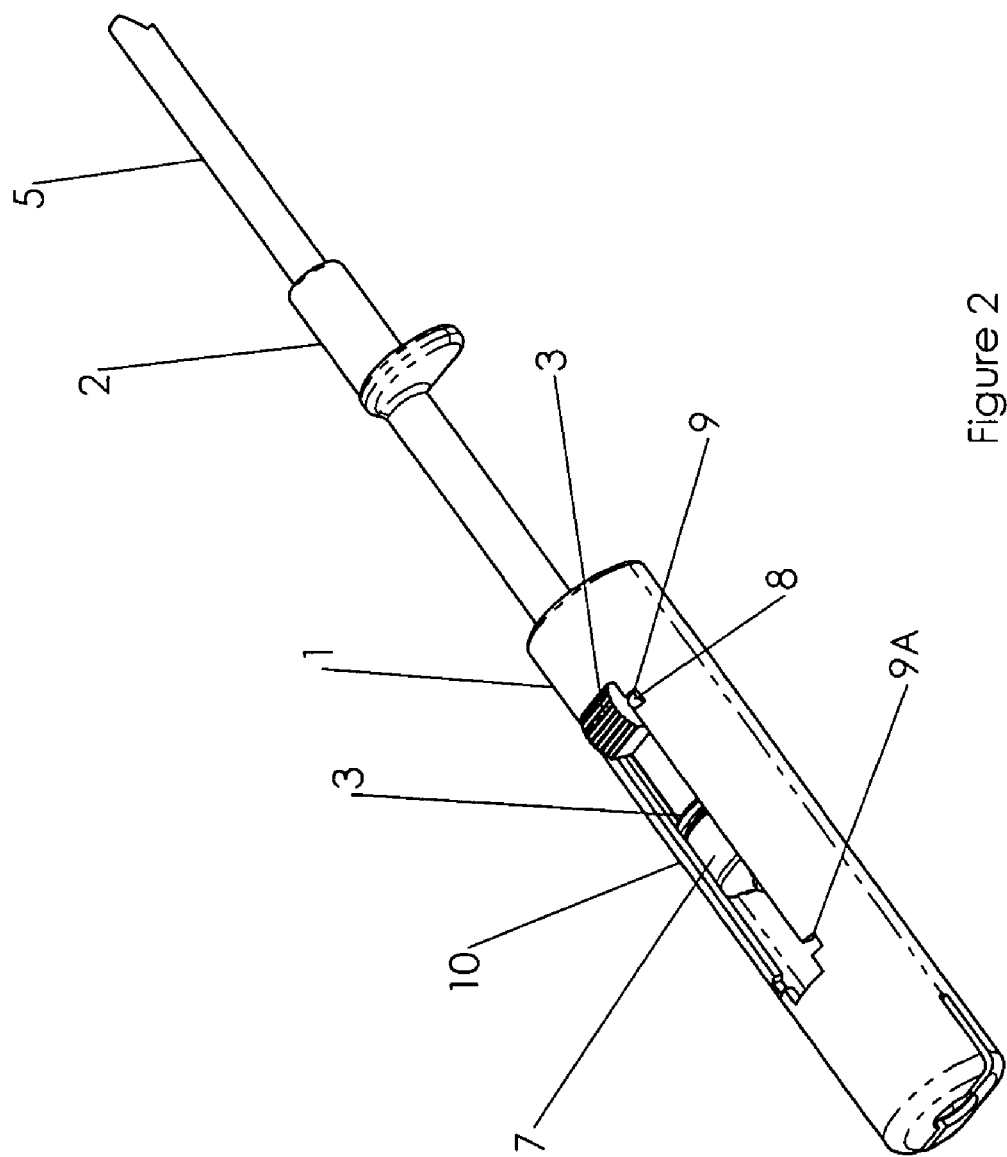
FIG. 2 shows the device in the fully retracted position.

In FIG. 2 the device is shown in the stowed mode as for shipment with the catheter and needle fully retracted into the sheath 1 and the hypodermic needle locked into position by the needle locking tab 8 engaged in the needle locking slot 9. The catheter is fixed in a locked and stowed position by the catheter carrier 7.

FIG. 3 shows the device as it would be used delivering IV fluids to a patient with the catheter 4 fully extended and the hypodermic needle retracted into the sheath 1. The hypodermic needle is locked into the retracted position by the needle locking tab 8 engaged in the needle locking slot 9.

Referring now to FIGS. 4–7 details of the needle, needle carrier, catheter and catheter carrier in the stowed position carrier are shown. FIGS. 4 and 5 are plan views shown to provide an orientation basis for FIGS. 6 and 7 which are cross sectional views. In FIG. 7 the needle 6 and catheter 4 are placed in the stowed and safe position by sliding them longitudinally in the inner cavity of the protective sheath 1 to a position where the needle 6 and catheter 4 cannot be touched. The hypodermic needle 6 is securely fastened to the needle carrier 3 which is locked into position by actuator spring 14 applying pressure to needle locking tab 8 (FIG. 5) to needle locking slot 9 (FIG. 4), thereby preventing any further longitudinal movement. The spring 14 must be strong enough to bias the tab into the slot, otherwise a coiled spring (not shown) may be placed beneath the spring 14 to add force to bias the tab into the slot.

As shown in FIG. 6 the catheter 4 is securely fastened to the catheter carrier 7. The catheter carrier 7 is connected to the needle carrier 3 by the forward retainer spring 26 on the needle carrier 3 engaging an interference fit between the forward locking surface 27 on the forward retainer spring 26 and the catheter locking surface 30 on the catheter carrier 7.

Referring now to FIGS. 8–11 details of the needle, needle carrier, catheter and catheter carrier in the exposed position are shown. As shown in FIG. 8 the hypodermic needle 6 and catheter 7 are moved to the fully extended position along with port body 2 by depressing actuator 11 against the force of the actuator spring 14 to disengage the needle locking tab 8 (FIG. 9) from the needle locking slot 9 allowing the needle carrier 3 and the catheter carrier 7 to slide longitudinally within the confines of the needle carrier track 10 (FIG. 10) and in the inner cavity of the protective sheath 1, to a position where the needle locking tab 8 can engage and lock the forward needle locking slot 9A.

Referring now to FIG. 10, the conical ramp 31 located on catheter carrier 7 deforms the molded shape of the protective sheath 1, relieved by, as best shown in FIG. 17, the retainer ring relief slot 22, to allow the catheter retainer slot 17, a molded feature of the catheter carrier 7, to lock into the carrier retainer ring 21, a molded feature of the protective sheath 1. In this longitudinally locked exposed position the hypodermic needle 6 and catheter can pierce a vein and start an IV injection. The catheter 4 has catheter taper 20 to allow a less painful insertion into the vein. As an indication that a vein has been entered, blood under pressure flows through the hypodermic needle 6 along the flashback blood path 23 and id absorbed in an absorbent indicator 13 located in the flashback sight tube 12. The flashback sight tube 12 is molded from clear plastic and can be viewed through the opening in the needle carrier track 10 as shown in FIG. 8.

With the hypodermic needle 6 in the extended position no IV fluid can flow due to the close fit between the hypodermic needle 6 and the catheter 4. This allows the IV fluids to be connected to the device before a vein is pierced. Air can be purged from the system prior to the application of the IV needle.

Referring now to FIG. 11 when the needle carrier 3 and the catheter carrier 7 is in the fully extended and locked position, the forward retainer spring 26 slides onto the needle carrier release ramp 29 located on the needle carrier release tab 28, a molded feature of the protective sheath 1, and disengages the forward locking surface 27 from the forward catheter locking surface 30. This allows the needle carrier 3 to be retracted separately from the catheter carrier 7. The catheter carrier 7 and the catheter 4 remain locked, extended and in the vein.

Referring now to FIGS. 12–16 the operation of the device with the needle in the retracted position is shown. The hypodermic needle 6 is moved to the fully retracted position by depressing actuator 11 against the force of the actuator spring 14 to disengage the needle locking tab 8 from the needle locking slot 9A allowing the needle carrier 3 to slide longitudinally constrained by the needle carrier track 10 and in the inner cavity of the protective sheath 1 to a position where the needle locking tab 8 can engage needle locking slot 9. The rear retainer tab 15 located on the needle carrier 3 snaps into the rear retainer slot 33 located on the port body 2. The needle carrier 3 is retained by this patient tamper proof mechanism formed by the rear retainer tab 15 and rear retainer slot 33.

With the needle carrier 3 and the hypodermic needle 6 in the retracted position and the catheter in the extended position, the hypodermic needle 6 no longer passes through the membrane 18. This membrane, made from an elastomer, allows an elastic aperture, formed by the initial hypodermic needle 6 penetration, to close.

Referring now to FIGS. 15 and 16 the membrane 18 forms a seal as the hypodermic needle 6 is removed and also forms a compressed gasket seal between the catheter carrier 7 and the port body 2. This seal is maintained by the locking ramp 35 on opposing sides of the port body 2 coming into contact with the port body retainer surface 34, creating a snap interference fit to compress membrane 18 at the contact surfaces.

When the hypodermic needle 6 is in the retracted position the IV fluids are free to flow in the flow cavity 16 along flow path 32, through the IV tube 5, through the port body 2, through membrane aperture 25 (best seen on FIG. 18) through catheter carrier 7 and catheter 4 to the vein.

The invention claimed is:

1. A catheter device comprising:
   a hollow protective sheath having a longitudinal needle carrier track long one surface and locking slots near either end of said track;
   a hypodermic needle carrier slidable mounted within said sheath to expose a hypodermic needle mounted and catheter mounted thereon and retract said hypodermic needle;
   an actuator mounted on said needle carrier and extending through said needle carrier track;
   needle locking tabs on the sides of said actuator for engagement with said locking slots;
   a spring connecting said actuator to said needle carrier biasing said actuator outwardly to force said needle locking tabs to engage either of said locking slots;
   a hypodermic needle mounted on said hypodermic needle carrier and extending longitudinally in said sheath;
   a catheter carrier and catheter releasably connected to said hypodermic needle carrier such that said hypodermic needle extends through said catheter; and
   a fluid flow path through said device that by-passes said hypodermic needle when retracted to said catheter when exposed.

2. The catheter device according to claim 1 further comprising a port body connected to said catheter carrier.

3. The catheter device according to claim 2 wherein said flow path passes through said port body, said flow aperture, said catheter carrier and said catheter when said catheter is exposed and said hypodermic needle is retracted.

4. The catheter device according to claim 1 wherein said catheter carrier is releasably connected to said hypodermic needle carrier by a forward retainer spring on said hypodermic needle carrier engaged to a forward retainer surface on said catheter carrier.

5. The catheter device according to claim 4 wherein said protective sheath further comprises a needle carrier release ramp on a needle carrier release tab molded into the internal surface thereof.

6. The catheter device according to claim 4 wherein said catheter carrier further comprises a catheter retainer slot which and said protective sheath further comprises a catheter retainer ring molded into the internal surface thereof.

7. The catheter device according to claim 6 further comprising a membrane interposed between said hypodermic needle carrier and said catheter carrier, said hypodermic needle piercing said membrane when said needle carrier and said catheter are in the retracted position, said membrane having a flow aperture between said port body and said catheter carrier.

8. The catheter device according to claim 7 wherein said flow aperture is blocked when said catheter carrier is connected to said needle carrier.

9. A catheter device comprising:
   a protective sheath;
   a hypodermic needle carrier slidable mounted in said protective sheath;
   a hypodermic needle mounted on said hypodermic needle carrier;
   a catheter carrier and catheter releasably mounted on said hypodermic needle carrier such that said hypodermic needle extends through said catheter;
   a port body connected to said catheter carrier for connection to an IV fluid source; and
   an IV fluid flow path through said port body, said catheter carrier and said catheter, said flow path being blocked by said hypodermic needle carrier when said catheter is mounted on said hypodermic needle carrier and open when said catheter carrier is released from said hypodermic needle carrier.

* * * * *